US009600631B2

(12) United States Patent
Stuart et al.

(10) Patent No.: US 9,600,631 B2
(45) Date of Patent: Mar. 21, 2017

(54) REMOTE PRESENCE SYSTEM INCLUDING A CART THAT SUPPORTS A ROBOT FACE AND AN OVERHEAD CAMERA

(71) Applicant: INTOUCH TECHNOLOGIES, INC., Goleta, CA (US)

(72) Inventors: David Stuart, Santa Barbara, CA (US); Daniel Steven Sanchez, Summerland, CA (US); Fuji Lai, Goleta, CA (US); Kevin Hanrahan, Santa Barbara, CA (US); Charles S. Jordan, Santa Barbara, CA (US); David Roe, Santa Barbara, CA (US); James Rosenthal, Santa Barbara, CA (US); Amante Mangaser, Goleta, CA (US); Blair Whitney, Santa Barbara, CA (US); Derek Walters, Campbell, CA (US)

(73) Assignee: INTOUCH TECHNOLOGIES, INC., Goleta, CA (US)

( * ) Notice: Subject to any disclaimer, the term of this patent is extended or adjusted under 35 U.S.C. 154(b) by 0 days.

(21) Appl. No.: 14/743,733

(22) Filed: Jun. 18, 2015

(65) Prior Publication Data
US 2015/0286789 A1 Oct. 8, 2015

Related U.S. Application Data

(63) Continuation of application No. 14/157,470, filed on Jan. 16, 2014, now Pat. No. 9,089,972, which is a (Continued)

(51) Int. Cl.
G05B 19/04 (2006.01)
G05B 19/18 (2006.01)
(Continued)

(52) U.S. Cl.
CPC ........ *G06F 19/3418* (2013.01); *B25J 9/1689* (2013.01); *B25J 9/1697* (2013.01);
(Continued)

(58) Field of Classification Search
CPC ... G06F 19/321; G06F 19/3418; H04N 7/185; H04L 67/10; H04L 65/403; B25J 9/1689; B25J 9/1697
(Continued)

(56) References Cited

U.S. PATENT DOCUMENTS 5,153,833 A * 10/1992 Gordon ................. F16M 11/18
180/167
5,802,494 A * 9/1998 Kuno ....................... A61B 5/02
128/920
(Continued)

FOREIGN PATENT DOCUMENTS

| JP | 2001-088124 A | 4/2001 |
| JP | 2002-035423 A | 2/2002 |
| WO | 2011/109336 A3 | 9/2011 |

OTHER PUBLICATIONS

"NetMeeting", Online Available at <http://web.archive.orgjweb/2006041 723 555 5/http://transcriptions .english>, retrieved on Apr. 17, 2006, 2 pages.
(Continued)

Primary Examiner — Jaime Figueroa

(57) ABSTRACT

A tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone. The remote station can display video images captured by the robot camera and/or overhead camera. By way of example, the cart can be used
(Continued)

in an operating room, wherein the overhead camera can be placed in a sterile field and the robot face can be used in a non-sterile field. The user at the remote station can conduct a teleconference through the robot face and also obtain a view of a medical procedure through the overhead camera.

20 Claims, 5 Drawing Sheets

Related U.S. Application Data continuation of application No. 12/717,806, filed on Mar. 4, 2010, now Pat. No. 8,670,017.

(51) Int. Cl.
G06F 19/00 (2011.01)
H04N 7/18 (2006.01)
B25J 9/16 (2006.01)
H04L 29/06 (2006.01)
H04L 29/08 (2006.01)

(52) U.S. Cl.
CPC .......... *G06F 19/321* (2013.01); *H04L 65/403* (2013.01); *H04L 67/10* (2013.01); *H04N 7/185* (2013.01)

(58) Field of Classification Search
USPC .......................................... 700/245, 257, 259
See application file for complete search history.

(56) References Cited

U.S. PATENT DOCUMENTS

| | | | |
|---|---|---|---|
| 5,867,494 A | 2/1999 | Krishnaswamy et al. | |
| 6,292,713 B1 * | 9/2001 | Jouppi ................... | G06F 3/011 345/629 |
| 6,292,714 B1 | 9/2001 | Okabayashi | |
| 6,346,962 B1 * | 2/2002 | Goodridge ............... | H04N 7/15 348/14.03 |
| 6,411,055 B1 | 6/2002 | Fujita et al. | |
| 6,667,592 B2 | 12/2003 | Jacobs et al. | |
| 6,674,259 B1 | 1/2004 | Norman et al. | |
| 7,467,211 B1 | 12/2008 | Herman et al. | |
| 7,483,867 B2 | 1/2009 | Ansari et al. | |
| 8,384,755 B2 | 2/2013 | Wang et al. | |
| 8,612,051 B2 | 12/2013 | Norman et al. | |
| 8,780,165 B2 | 7/2014 | Wang et al. | |
| 8,994,776 B2 * | 3/2015 | Sutherland ............... | B25J 5/007 180/167 |
| 8,996,165 B2 * | 3/2015 | Wang ......................... | B25J 5/00 348/14.02 |
| 9,014,848 B2 * | 4/2015 | Farlow ................... | B25J 11/009 700/245 |
| 2002/0015296 A1 * | 2/2002 | Howell ................... | E04B 9/006 362/11 |
| 2002/0044201 A1 * | 4/2002 | Alexander ............... | H04N 7/15 348/14.08 |
| 2004/0243147 A1 * | 12/2004 | Lipow ................... | A61B 90/36 606/130 |
| 2004/0260790 A1 | 12/2004 | Balloni et al. | |
| 2005/0052527 A1 * | 3/2005 | Remy .................... | H04N 7/185 348/14.08 |
| 2006/0052676 A1 * | 3/2006 | Wang .................... | A61B 5/0006 600/300 |
| 2006/0119701 A1 * | 6/2006 | King ...................... | H04N 7/185 348/14.08 |
| 2006/0161303 A1 * | 7/2006 | Wang .................. | A61B 19/2203 700/259 |
| 2007/0176060 A1 * | 8/2007 | White ................ | A61B 19/0248 248/124.1 |
| 2008/0263628 A1 | 10/2008 | Norman et al. | |
| 2009/0173846 A1 | 7/2009 | Katz | |
| 2010/0100240 A1 * | 4/2010 | Wang ......................... | B25J 5/00 700/259 |
| 2011/0187875 A1 * | 8/2011 | Sanchez ............. | A61B 19/2203 348/207.11 |
| 2014/0267552 A1 | 9/2014 | Wang et al. | |
| 2014/0347269 A1 | 11/2014 | Ballantyne et al. | |

OTHER PUBLICATIONS

Supplementary European Search Report for EP Patent Application No. 07872529.8, mailed on Nov. 30, 2010, 9 pages.

Fulbright et al., "SWAMI: An Autonomous Mobile Robot for Inspection of Nuclear Waste of Storage Facilities", Autonomous Robots, 2, 1995, pp. 225-235.

* cited by examiner

REMOTE PRESENCE SYSTEM INCLUDING A CART THAT SUPPORTS A ROBOT FACE AND AN OVERHEAD CAMERA

BACKGROUND OF THE INVENTION

1. Field of the Invention

The subject matter disclosed generally relates to the field of robotic tele-presence systems.

2. Background Information

Robots have been used in a variety of applications ranging from remote control of hazardous material to assisting in the performance of surgery. For example, U.S. Pat. No. 5,762,458 issued to Wang et al. discloses a system that allows a surgeon to perform minimally invasive medical procedures through the use of robotically controlled instruments. One of the robotic arms in the Wang system moves an endoscope that has a camera. The camera allows a surgeon to view a surgical area of a patient.

There has been marketed a mobile tele-presence robot introduced by InTouch Technologies, Inc., the assignee of this application, under the trademark RP-7. The InTouch robot is controlled by a user at a remote station. The remote station may be a personal computer with a joystick that allows the user to remotely control the movement of the robot. Both the robot and remote station have cameras, monitors, speakers and microphones to allow for two-way video/audio communication. The robot camera provides video images to a screen at the remote station so that the user can view the robot's surroundings and move the robot accordingly.

InTouch also provides a system sold as VisitOR that includes a robot face that is attached to a boom. The boom and robot face can be installed into an operating room. Using a robot face in an operating room may require sterilization of the face. Additionally, the VisitOR requires the installation of a boom in the operating room. This can add to the cost and complexity of installing such a system.

BRIEF SUMMARY OF THE INVENTION

A tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone.

DETAILED DESCRIPTION

Disclosed is a tele-presence system that includes a cart. The cart includes a robot face that has a robot monitor, a robot camera, a robot speaker, a robot microphone, and an overhead camera. The system also includes a remote station that is coupled to the robot face and the overhead camera. The remote station includes a station monitor, a station camera, a station speaker and a station microphone. The remote station can display video images captured by the robot camera and/or overhead camera. By way of example, the cart can be used in an operating room, wherein the overhead camera can be placed above a sterile field to provide a more advantageous vantage point to view a procedure. The user at the remote station can conduct a teleconference through the robot face and also obtain a view of a medical procedure through the overhead camera.

Figure 1:
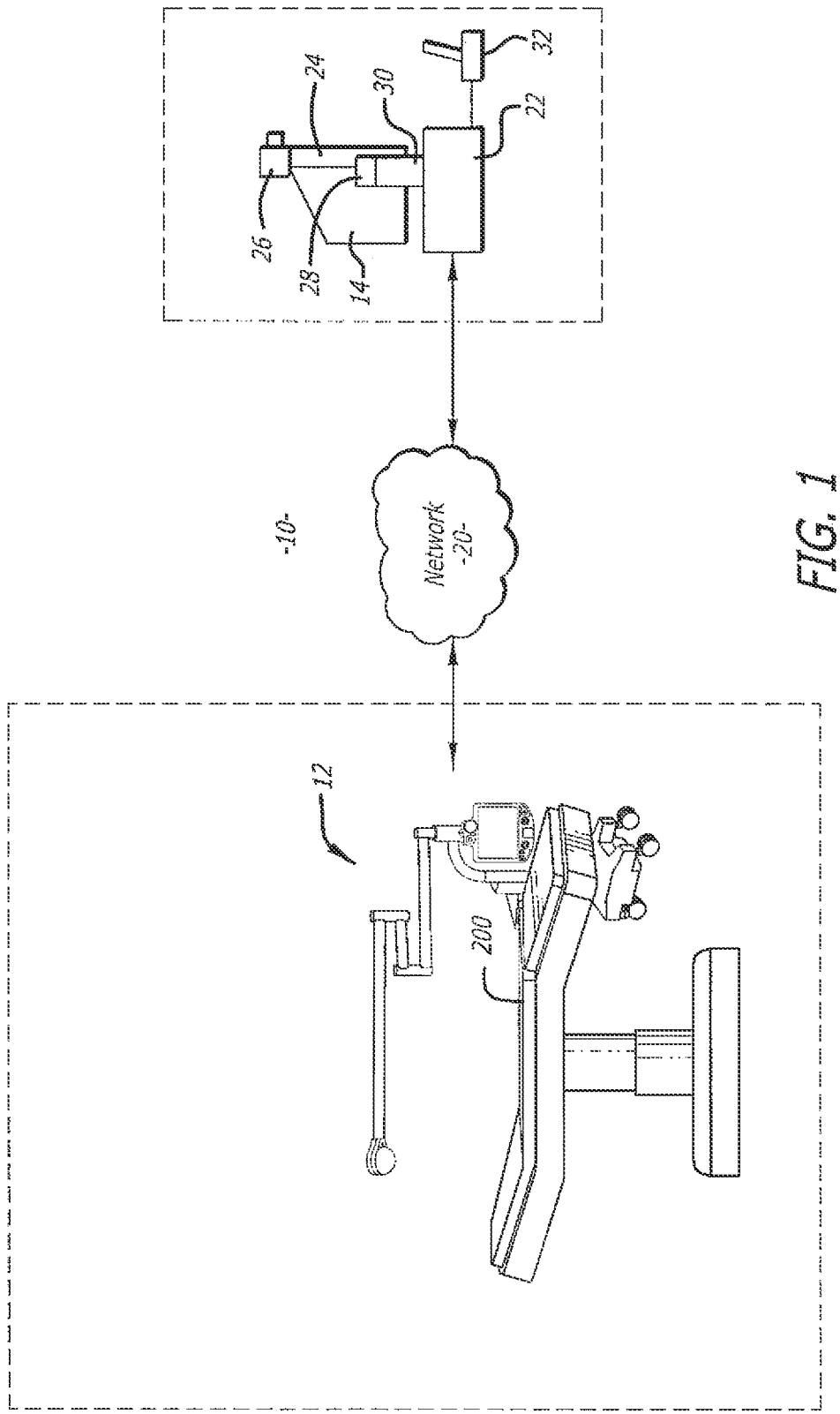
FIG. 1 is an illustration of a tele-presence system.
Figure 2:
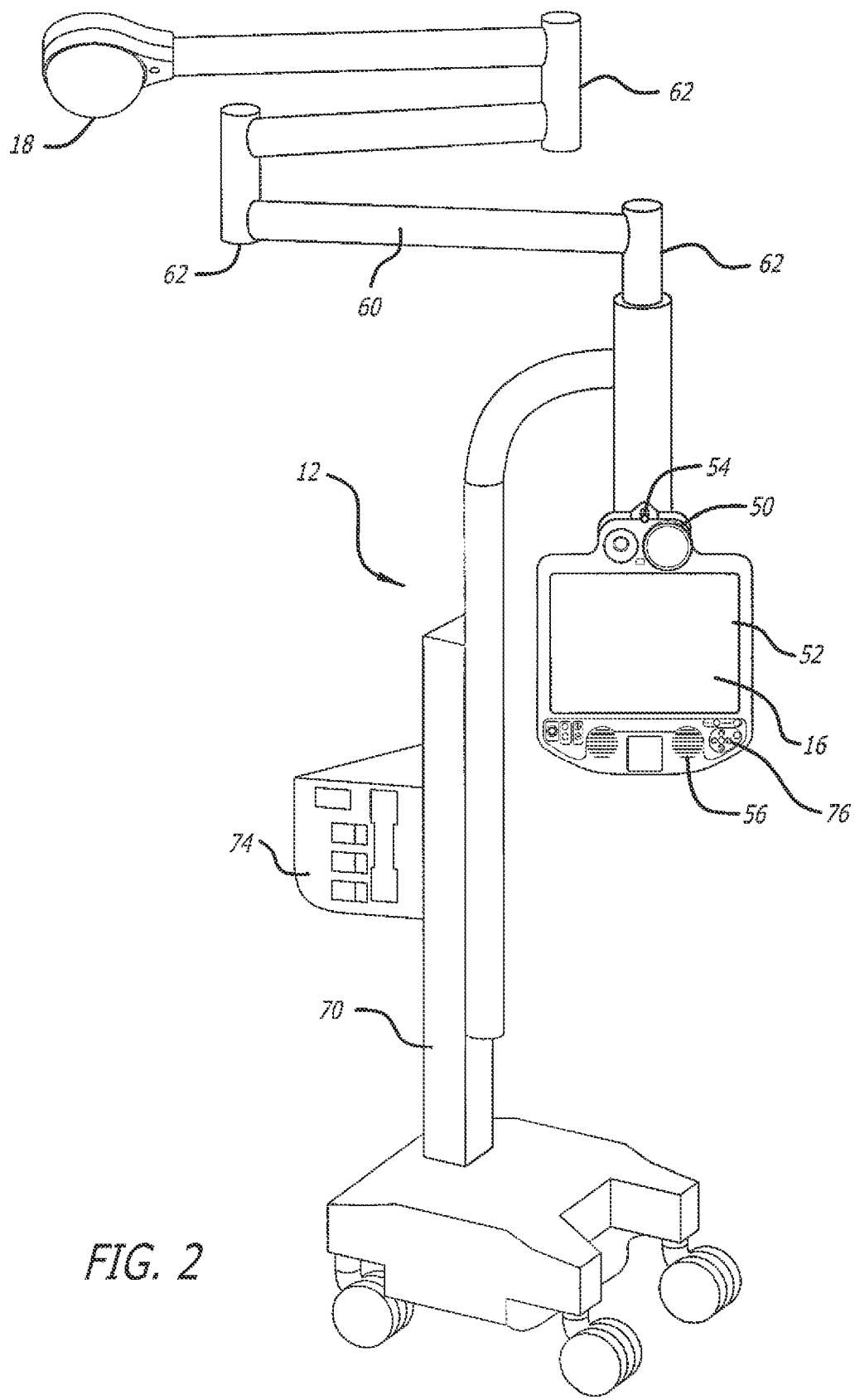
FIG. 2 is a perspective view of a cart of the system.
Figure 3:
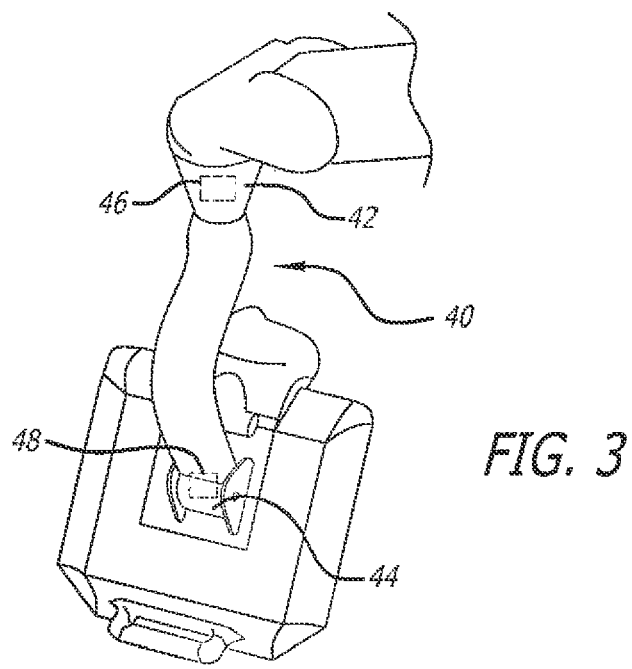
FIG. 3 is a rear view of an articulated arm and a robot face of the cart.

Referring to the drawings more particularly by reference numbers, FIGS. 1, 2 and 3 show a tele-presence system 10. The system 10 includes a cart 12 that is coupled to a remote control station 14. The cart 12 has a robot face 16 and an overhead camera 18. The remote control station 14 may be coupled to the cart 12 through a network 20. By way of example, the network 20 may be either a packet switched network such as the Internet, or a circuit switched network such as a Public Switched Telephone Network (PSTN) or other broadband system. Alternatively, the cart 12 may be coupled to the remote station 14 network thru a satellite.

The remote control station 14 may include a computer 22 that has a monitor 24, a camera 26, a microphone 28 and a speaker 30. The computer 22 may also contain an input device 32 such as a joystick or a mouse. The control station 14 is typically located in a place that is remote from the cart 12. Although only one remote control station 14 is shown, the system 10 may include a plurality of remote stations 14. In general any number of carts 12 may be coupled to any number of remote stations 14 or other carts 12. For example, one remote station 14 may be coupled to a plurality of carts 12, or one cart 12 may be coupled to a plurality of remote stations 14, or a plurality of carts 12. The system may include an arbitrator (not shown) that control access between the carts 12 and the remote stations 14.

As shown in FIG. 3, the cart 12 may include an articulated arm 40 that supports and can move the robot face 16. The articulated arm 40 may have active joints 42 and 44 that allow the robot face 14 to be panned and tilted, respectively. The active joints 42 and 44 may move in response to commands provided by the remote station. The joints 42 and 44 may contain position sensors 46 and 48, respectively, that provide positional feedback of the arm 40.

Referring to FIGS. 2 and 3, each robot face 16 includes a camera(s) 50, a monitor 52, a microphone(s) 54 and a speaker(s) 56. The robot camera 50 is coupled to the remote monitor 24 so that a user at the remote station 14 can view a video image captured by the robot camera 50. Likewise, the robot monitor 52 is coupled to the remote camera 26 so personnel at the surgical site may view the user of the remote station 14. The microphones 28 and 54, and speakers 30 and 56, allow for audible communication between the system operator and the personnel at the surgical site.

The overhead camera 18 may be coupled to a boom 60. The boom 60 may include a number of joints 62, either active or passive. The joints 62 may include positional sensors to provide feedback regarding the position of the overhead camera 18.

Figure 4:
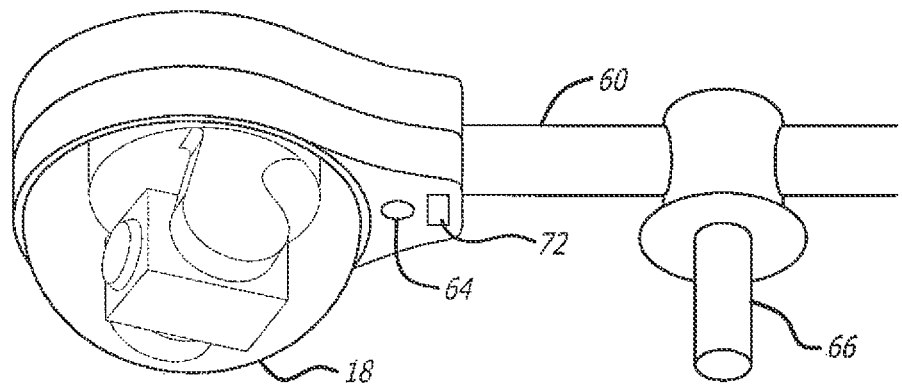
FIG. 4 is an enlarged perspective view of an overhead camera of the cart.

As shown in FIG. 4, the cart 12 may include an overhead microphone 64 and a detachable handle 66. The overhead microphone 64 may provide an alternative source of sound. The detachable handle 66 can be used to move the boom 60 and overhead camera 18. If the cart 12 is used in a sterile field, for example in an operating room, the handle 66 may be replaced with a sterile handle before each medical procedure to allow a surgeon within the sterile field to position the boom during a procedure.

Referring again to FIG. 2, the cart 12 may include a linear actuator 70 that can be remotely or locally actuated to vary the height of the robot face 16 and overhead camera 18. Varying the height allows the cart 12 to be rolled through doors and then actuated to move the face 16 and camera 18 to elevated positions. For example, the face 16 and camera 18 can be lowered to allow the cart 12 to be moved into an operating room. The camera 18 can then be raised to provide a desirable view over an operating table. The cart 12 may include a laser pointer 72 and/or directed lighting (not shown) located on the boom 60. The cart 12 may also include a local control panel 74 to move the articulated arm 40, actuator 70 and/or boom 60. The linear actuator 70 is also advantageous in moving the face 16 to be essentially at the same level as a person whether they are standing, sitting or lying in a prone position.

The robot face 16 may include a processor, hard disk drive and other circuits that enable the face 16 to function as a computer. The face 16 may include an input panel 76 that allows a user to provide input. By way of example, the operator of the remote station may provide one or more questions through the robot face 16, wherein a user of the cart provides answers through the input panel 76.

The system 10 may have certain components and software that are the same or similar to a robotic system provided by the assignee InTouch Technologies, Inc. of Goleta, Calif. under the name RP-7 and embodies a system described in U.S. Pat. No. 6,925,357, which is hereby incorporated by reference.

Figure 5:
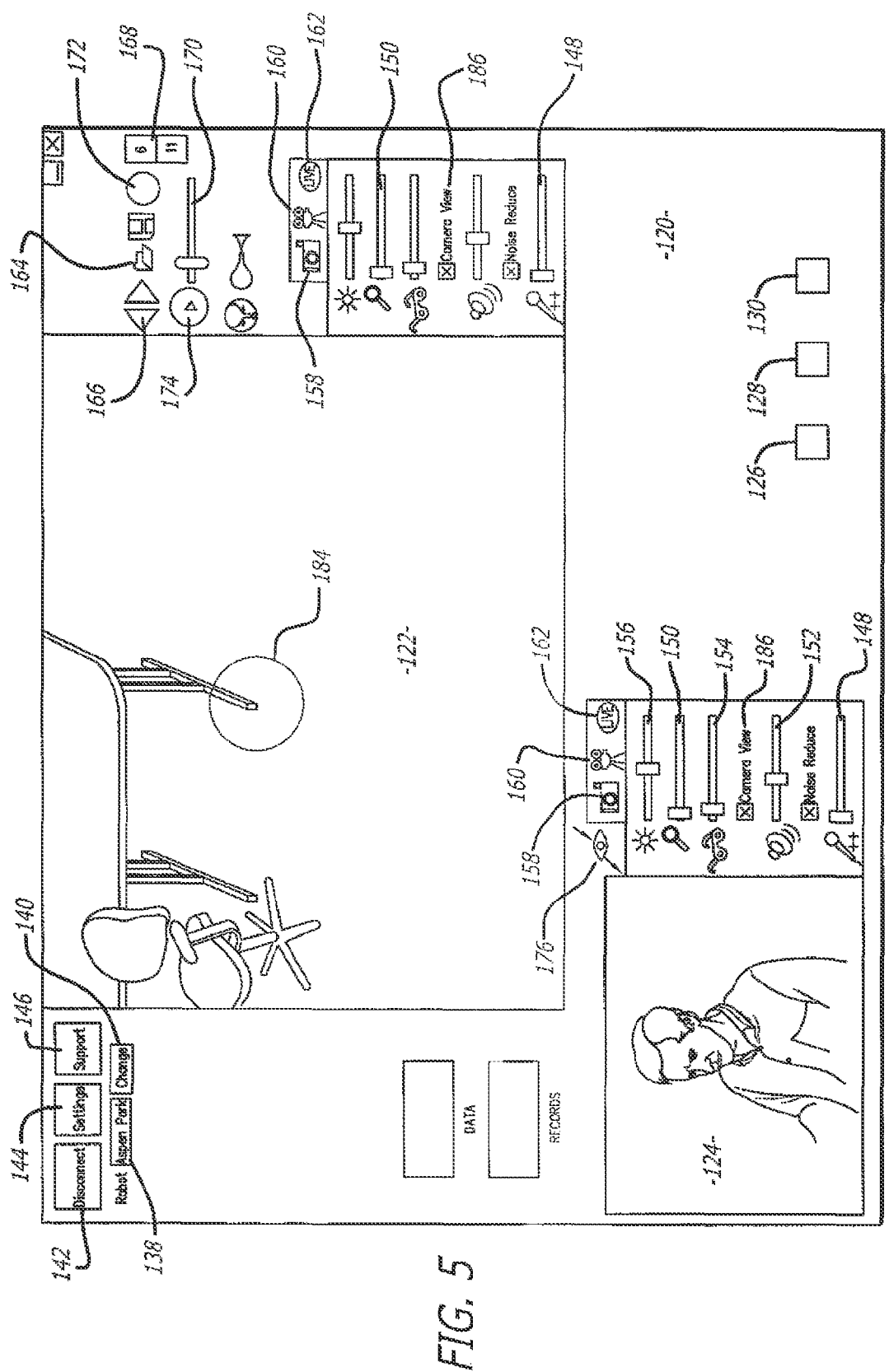
FIG. 5 is an illustration of a display user interface of a remote station.

FIG. 5 shows a display user interface ("DUI") 120 that can be displayed at the remote station 14. The DUI 120 may include a robot view field 122 that displays a video image captured by the robot camera and/or the overhead camera. The DUI 120 may also include a station view field 124 that displays a video image provided by the camera of the remote station 14. The DUI 120 may be part of an application program stored and operated by the computer 22 of the remote station 14.

Figure 6:
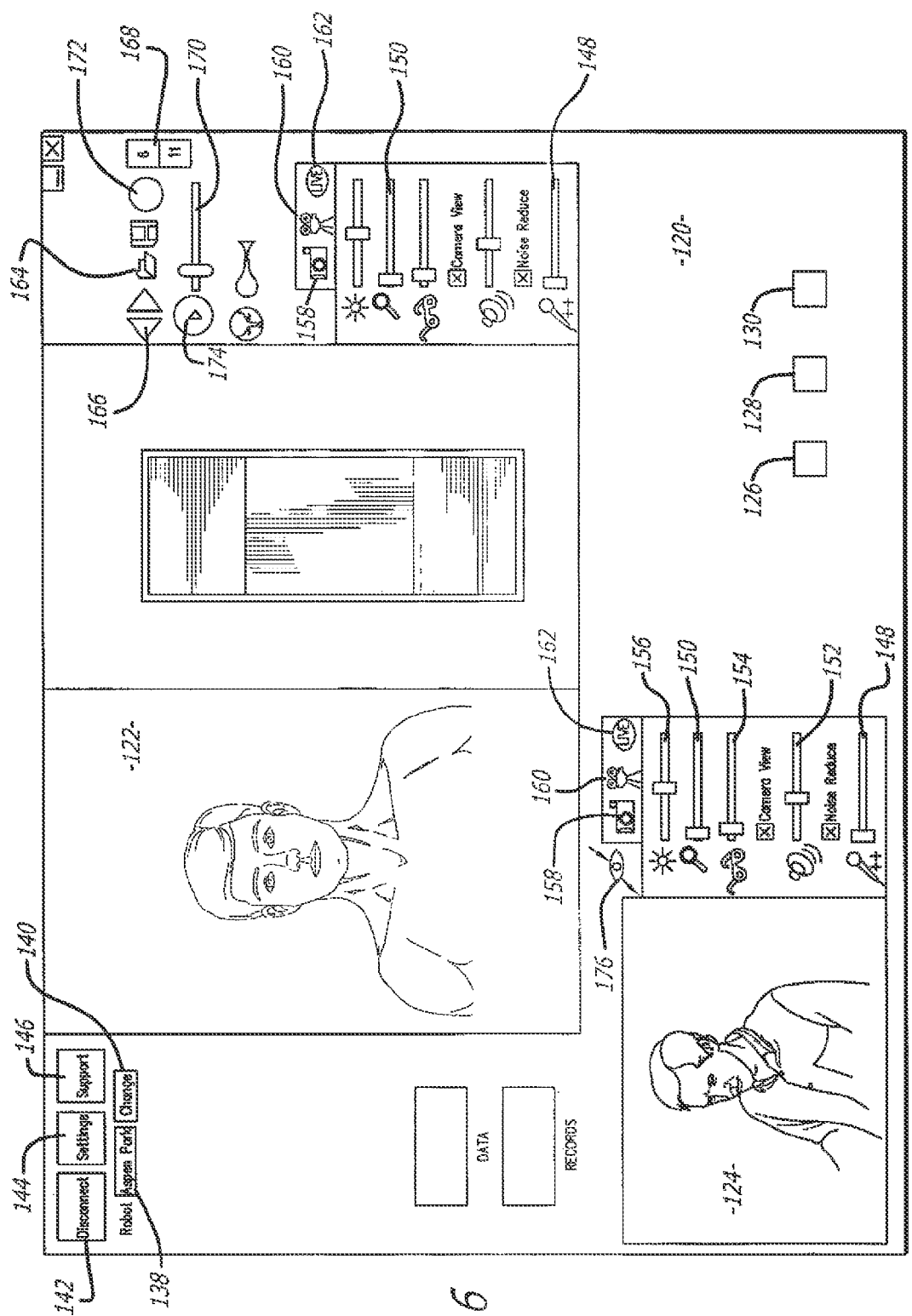
FIG. 6 is an illustration of the display user interface showing video images captured by a robot camera and an overhead camera being simultaneously displayed.

The DUI 120 may include a graphical switch 126 that allows the user to select between the video image provided by the robot camera and the video image provided by the overhead camera. The DUI 120 may also have a graphical switch 128 that allows the user to select the simultaneous display of the video images from the robot and overhead cameras as shown in FIG. 6. The video images from both cameras can be streamed to the remote station from the cart. The images can be merged by presenting a center rectangle of each image (e.g., 320×480 center area). A zoom or highlighting feature may be utilized by manipulating a cursor on either image. The system may also automatically pan a camera when the cursor is moved out of the displayed field of view.

The system may automatically present the video image from a camera that has an optimal view of an object. For example, the system may utilize pattern recognition techniques to determine which video image provides a more clear image of an object. The system may determine which camera is in closer proximity to an object and provide the image from the camera that is closer to the object. The system may utilize positional feedback from the cart to determine the proximity of the cameras relative to the object. The system may also have sensors, such as laser, sonar, etc. that can determine the proximity of the cameras to the object. The system may use the feedback and/or sensors to determine which camera is closer to an object.

The system may automatically move the cameras so that each camera is pointed to the same or substantially the same field of view. For example, if the robot face is pointed toward an object, the overhead camera can be automatically moved to capture a video image of the same object. Likewise, if the overhead camera is capturing a video image of an object, the robot face can be automatically moved to point toward the same object. This enhances the "presence" of the remote operator because they are facing the same object that the overhead camera is viewing.

The DUI 120 may have a graphical switch 130 that allows the user to switch between sound captured by the robot microphone or the overhead microphone. The system may automatically switch between microphones based on a characteristic(s) of the sound captured by the microphones. For example, the system may switch to the microphone that provides the highest aural clarity, or to the microphone that is in the closest proximity to a person or object generating the sound.

The DUI 120 may include a location display 138 that provides the location of the robot face. The CHANGE button 140 can be selected to change the default robot face in a new session. The CHANGE button 140 can be used to select and control a different robot face in a system that has multiple robot faces. The user can initiate and terminate a session by selecting box 142. The box 142 changes from CONNECT to DISCONNECT when the user selects the box to initiate a session. System settings and support can be selected through buttons 144 and 146.

Both the robot view field 122 and the station view field 124 may have associated graphics to vary the video and audio displays. Each field may have an associated graphical audio slide bar 148 to vary the audio level of a selected microphone and another slide bar 152 to vary the volume of the speakers.

The DUI 120 may have slide bars 150, 154 and 156 to vary the zoom, focus and brightness of a selected camera, respectively. A still picture may be taken at either the robot face or remote station by selecting one of the graphical camera icons 158. The still picture may be the image presented at the corresponding field 122 or 124 at the time the camera icon 158 is selected. Capturing and playing back video can be taken through graphical icons 160. A return to real time video can be resumed, after the taking of a still picture, captured video, or reviewing a slide show, by selecting a graphical LIVE button 162.

A still picture can be loaded from disk for viewing through selection of icon 164. Stored still images can be reviewed by selecting buttons 166. The number of the image displayed relative to the total number of images is shown by graphical boxes 168. The user can rapidly move through the still images in a slide show fashion or move through a captured video clip by moving the slide bar 170. A captured video image can be paused through the selection of circle 174. Play can be resumed through the same button 174. Video or still images may be dismissed from the active list through button 172. Video or still images may be transferred to the robot by selecting icon 176. For example, a doctor at the remote station may transfer an x-ray to the screen of the robot.

The system may provide the ability to annotate 184 the image displayed in field 122 and/or 124. For example, a doctor at the remote station may annotate some portion of the image captured by the robot face camera. The annotated image may be stored by the system. The system may also allow for annotation of images sent to the robot face through icon 176. For example, a doctor may send an x-ray to the robot face which is displayed by the robot screen. The doctor can annotate the x-ray to point out a portion of the x-ray to personnel located at the robot site. This can assist in allowing the doctor to instruct personnel at the robot site.

The display user interface may include graphical inputs 186 that allow the operator to turn the views of the remote station and remote cameras on and off.

Referring to FIG. 1, the cart 12 can be used in an operating room. By way of example, the boom 60 can be moved to place the overhead camera 18 above an operating table 200. The overhead camera 18 may be located above a sterile field. The robot face 16 may be placed adjacent to the sterile field. With such a configuration, personnel may conduct two-way video conferencing through the robot face 16. The overhead camera 18 may provide a more desirable view of the patient and operating procedure. This would allow a physician at the remote station to view the procedure and have a video conference to provide instructions, mentoring, etc. to personnel at the surgical site.

While certain exemplary embodiments have been described and shown in the accompanying drawings, it is to be understood that such embodiments are merely illustrative of and not restrictive on the broad invention, and that this invention not be limited to the specific constructions and arrangements shown and described, since various other modifications may occur to those ordinarily skilled in the art.

What is claimed is:

1. A tele-presence system, comprising:
    a cart that supports a boom, an overhead camera coupled to the boom, a mechanism that allows the height of the boom to be varied, and a robot face that has a robot monitor, a robot camera, a robot speaker, and a robot microphone; and,
    a remote station that is coupled to said robot face and said overhead camera, said remote station includes a station monitor, a station camera, a station speaker and a station microphone, wherein at least one of the robot camera and the overhead camera can be controlled from the remote station.

2. The system of claim 1, wherein said remote station can display a video image from either said robot camera or said overhead camera.

3. The system of claim 1, wherein said remote station monitor simultaneously displays a video image from said robot camera and a video image from said overhead camera.

4. The system of claim 1, wherein said cart includes an overhead microphone.

5. The system of claim 4, wherein said remote station includes an input that allows a user to switch between said robot microphone and said overhead microphone.

6. The system of claim 1, wherein said cart includes an actuator that can vary a height of said robot face.

7. The system of claim 1, wherein said cart includes an articulated arm that is coupled to and can move said robot face.

8. The system of claim 7, wherein said robot face includes an input panel and can be operated as a computer.

9. The system of claim 7, wherein further comprising a laser pointer attached to said boom.

10. The system of claim 7, wherein said boom includes a detachable handle.

11. A method for remotely viewing a field of view, comprising:
    moving a cart that supports a boom, an overhead camera coupled to the boom, a mechanism that allows the height of the boom to be varied, and a robot face that has a robot monitor, a robot camera, a robot speaker, and a robot microphone; varying the height of the boom supported by the cart;
    transmitting to a remote station a video image captured by the robot camera or a video image captured by the overhead camera, the remote station includes a station monitor, a station camera, a station speaker and a station microphone; and,
    controlling at least one of the robot camera and the overhead camera from the remote station.

12. The method of claim 11, wherein the video images captured by the robot and overhead cameras are both transmitted to the remote station.

13. The method of claim 12, wherein the remote station monitor simultaneously displays the video image from the robot camera and the video image from the overhead camera.

14. The method of claim 11, further comprising capturing sound with an overhead microphone of the cart.

15. The method of claim 14, further comprising selecting an input to switch between the robot microphone and the overhead microphone.

16. The method of claim 11, further comprising varying a height of the robot face.

17. The method of claim 16, wherein the robot face is moved in two degrees of freedom.

18. The method of claim 11, further comprising moving the overhead camera above a sterile field.

19. The method of claim 11, further comprising entering input into the robot face.

20. The method of claim 11, further comprising replacing a detachable handle of the cart.

* * * * *